United States Patent
Lensky et al.

(10) Patent No.: US 6,344,471 B1
(45) Date of Patent: Feb. 5, 2002

(54) 2-AMINOCARBONYL-5(2H)-ISOXAZOLONES AS LIGANDS OF A DFP-BINDING SITE TREATMENT OF CNS-DISEASES

(75) Inventors: Stephan Lensky, Kürten; Bernd Riedl, Wuppertal; Chantal Fürstner, Mülheim an der Ruhr; Jens Ergüden; Frank Böss, both of Wuppertal; Bernhard Schmidt, Lindlar; Franz-Josef van der Staay, Lohmar-Wahlscheid; Werner Schröder, Wuppertal; Joachim Schuhmacher, Wuppertal; Delf Schmidt, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/720,024

(22) PCT Filed: Jun. 11, 1999

(86) PCT No.: PCT/EP99/04030

§ 371 Date: Feb. 27, 2001

§ 102(e) Date: Feb. 27, 2001

(87) PCT Pub. No.: WO99/67229

PCT Pub. Date: Dec. 29, 1999

(30) Foreign Application Priority Data

Jun. 19, 1998 (DE) .......................... 198 27 387

(51) Int. Cl.[7] ........................ A61K 31/42; C07D 413/06
(52) U.S. Cl. ........................... 514/380; 548/243
(58) Field of Search ........................... 548/243; 514/380

(56) References Cited

FOREIGN PATENT DOCUMENTS

BE 791903 5/1973

OTHER PUBLICATIONS

Millan, D. S., and Prager, R. H., "The chemistry of 5–oxodihydroisoxazoles. Part 22.[1] The synthesis of 1,3–oxazin–6–ones from N–thioacylisoxazol–5(2H)–ones", J. Chem. Soc. Perkin Trans. 1, pp. 3245–3252 (1998).

Chem. Abstr., vol. 83, No. 28, p. 555 (1975), 114366t; Tomita, K., Murakami, T., Takagi, H., Morisawa, Y. (Sankyo Co. Ltd.), "Isoxazolinone Derivatives", JP 74 72251, Jul. 12, 1974.

Ellman, G. L., Courtney, K. D., Andres, Jr. V., and Featherstone, R. M., "A New and Rapid Colorimetric Determination of Acetylcholinesterase Activity", Biochem. Pharmacol., 7: 88–95(1961).

Konno, N., Suzuki, N., Horiguchi, H., and Fukushima, M., "Characterization of High–affinity Binding Sites for Diisopropylfluorophophate (DFP) from Chicken Spinal Cord Membranes", Biochem. Pharmacol., 48(11): 2073–2079 (1994).

Lassalvy, C., Petrus, C., and Petrus, F., "Action de l'hydroxyuuree sur les esters α–acyleniques", Can. J. Chem., 59: 175–179 (1981).

Morris, R., "Developments of a water–maze procedure for studying spatial learning in the rat", J. Neuroscience Methods, 11: 47–60 (1984).

Porsolt, R. D., Le Pichon, M., Jalfree, M., "Depression: a new animal model sensitive to antidepressant treatments", Nature, 266: 730–732 (Apr. 1977).

Schmidt, B. H., Hinz, V. C., and Van Der Staay, F. J., "Cognition Enhancement by Metrifonate: Evidence from Animal Studies", Alzheimer's Disease: Biology, Diagnosis and Therapeutics, Iqbal et al., eds., (1997) John Wiley & Sons Ltd., pp. 781–786.

Van Der Staay, F. J., Hinz, V. Ch., and Schmidt, B. H., "Effects of Metrifonate, its Transformation Product Dichlorvos, and other Organophosphorus and Reference Cholinesterase Inhibitors on Morris Water Escape Behavior in Young–Adult Rats", J. Pharmcol. & Exp. Ther., 278(2): 697–708 (1996).

Wierenga, W., Evans, B. R., and Zurenko, G. E., "Benzisoxazolones: Antimicrobial and Antileukemic Activity", J. Med. Chem., 27: 1212–1215 (1984).

*Primary Examiner*—Robert Gerstl
(74) *Attorney, Agent, or Firm*—Jerrie L. Chiu

(57) ABSTRACT

The present invention relates to novel 2-aminocarbonyl-5 (2H)-isoxazolones as selective ligands of a high-affinity binding site of diisopropyl fluorophosphate (DFP) on brain membranes for the prophylaxis and treatment of disorders of the central nervous system, in particular cognitive disorders, depression, schizophrenia and anxiety.

9 Claims, No Drawings

2-AMINOCARBONYL-5(2H)-ISOXAZOLONES AS LIGANDS OF A DFP-BINDING SITE TREATMENT OF CNS-DISEASES

The present invention relates to novel 2-aminocarbonyl-5(2H)-isoxazolones as selective ligands of a high-affinity binding site of diisopropyl fluorophosphate (DFP) on brain membranes for the prophylaxis and treatment of disorders of the central nervous system, in particular cognitive disorders, depression, schizophrenia and anxiety.

Studies with the so-called Morris test, an animal model for learning and memory, have shown that diisopropyl fluorophosphate (DFP) has an enhancing effect on learning and memory processes (J. Pharmacol. Exp. Ther. 1996, 278, 697–708). The optimum dosage of DFP for the procognitive effect in young adult rats is 0.03 mg/kg, administered orally. An increase of the dose above this value does not lead to a further increase in learning performance, but to a return to the control level and, when increased even further, to a deterioration of the cognitive performance compared to control animals. DFP does indeed inhibit cholinesterase; however, a significant cholinesterase inhibition in the brain of rats ex vivo is achieved only at dosages of $\geq 3$ mg/kg orally, i.e. at dosages which are higher by a factor of about 100 than the active dose in the learning test. Cholinesterase inhibitors such as tacrine or physostigmine, which differ structurally from phosphoric acid esters, show no improvement of cognitive learning ability in this animal model.

The discrepancy between the cognitively stimulating dosages on the one hand and acetylcholinesterase-inhibiting dosages on the other hand indicates that a second mechanism of action, which is more sensitive for DFP than cholinesterase, is involved.

In the spinal cord of chicken, a high-affinity binding site for DFP has been identified (Biochem. Pharmacol. 1994, 48, 2073–2079), which differs from the catalytically active centres of acetylcholinesterase and butyrylcholinesterase. The function of the novel high-affinity binding site for DFP has hitherto not been known.

For the first time, it has now been found that high-affinity specific binding sites for DFP are present in membranes of the mammal brain. They were demonstrated in membranes of the cerebral cortex of rat, calf and man.

Surprisingly, the high-affinity binding site for DFP is not a known molecular target of DFP. In particular, the competition profile of the binding site does not agree with that of acetylcholinesterase, butyrylcholinesterase, neuropathy target esterase, prolylendopeptidase and dipeptidyl peptidase II. Moreover, selective ligands for 84 known neurotransmitter receptors, enzymes and ion channels of the mammal brain were tested in vitro for [$^3$H]DFP competition. None of the compounds showed any affinity, not even at very high concentrations which were already physiologically irrelevant.

In addition to DFP, only the known acetylcholinesterase inhibitor dichlorvos binds to the high-affinity DFP binding site.

Accordingly, cerebral tissue preparations of mammals, preferably of rat, calf or human, are suitable for finding ligands of the high-affinity DFP binding site.

The high-affinity DFP binding site is isolated by customary methods from cerebral tissue of mammals, preferably by homogenization and centrifugation of the tissue, and resuspension of the precipitate.

The ligand is then generally added in various concentrations to this mixture and preincubated.

To measure binding, DFP is added, and the mixture is incubated. The DFP is usually labelled, preferably radioactively labelled. DFP is added in concentrations of less than 50 nM, preferably in a concentration of 0.1 –20 nM, very particularly preferably 5–15 nM.

Ligands are usually understood as meaning modulators, i.e. substances which influence the activity of the binding site. The modulators can act agonistically or antagonistically on the binding site.

Binding sites in the context of the invention are endogenous proteins, preferably enzymes or receptors.

The learning- and memory-enhancing effect of DFP described above is explained by the properties of the novel high-affinity binding site for DFP. Accordingly, substances which influence this binding site like DFP should also have the cognition-enhancing effect of DFP. Such substances are therefore suitable both for therapeutic and preventive treatment of cognitive disorders in general, in particular of dementias of the Alzheimer type.

Moreover, the antimicrobial and antileukaemic effect of 1-(1-amninocarbonyl)-2,1-benzisoxazol-3(1H)-ones is known (J. Med. Chem. 1984, 27, 1212–1215). The synthesis of 2-aminocarbonyl-3-methyl-5(2H)-isoxazolone has also been described (Can. J. Chem. 1981, 59, 175–179).

The present invention relates to compounds of the general formula (I)

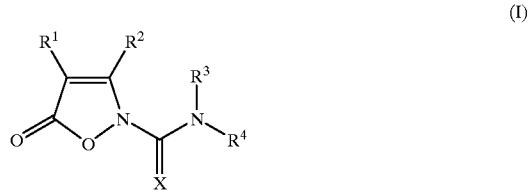

in which
$R^1$ and $R^2$ are identical or different and
represent $(C_1-C_8)$-alkyl which is optionally interrupted by an oxygen or sulphur atom or by a radical $NR^5$ and which is optionally mono- or polysubstituted by radicals selected from the group consisting of $(C_1-C_4)$-alkoxy, $(C_1-C_3)$-perfluoroalkoxy, halogen and $NR^6R^7$,
represent $(C_3-C_8)$-cycloalkyl which is optionally interrupted by an oxygen or sulphur atom or by a radical $NR^8$ and which is optionally mono- or polysubstituted by radicals selected from the group consisting of $(C_{1-C4})$-alkoxy, $(C_1-C_3)$-perfluoroalkoxy, halogen and $NR^9R^{10}$,
represent aryl-$(CH_2)_m$,
in which
$R^5$, $R^6$, $R^7$, $R^8$, $R^9$ and $R^{10}$ are identical or different and independently of one another represent hydrogen, $(C_1-C_4)$-alkyl, $(C_1-C_4)$-acyl, $(C_1-C_4)$-alkoxy-carbonyl, carbamoyl, mono- or di-$(C_1-C_4)$-alkyl-amino-carbonyl, and
m represents 0, 1, 2 or 3, or
$R^1$ represents hydrogen, aryl-$S(O)_n$, $(C_1-C_4)$-alkoxy, aryl-O or halogen and
$R^2$ is as defined above, and
in which
n represents 0, 1 or 2, or
$R^1$ and $R^2$ together with the adjacent carbon atoms form a 5- to 10-membered monounsaturated carbocycle which is optionally interrupted by an oxygen or sulphur atom or by a radical $NR^{11}$ and which is optionally mono- or polysubstituted by radicals selected from the group consisting of $(C_1-C_4)$-alkoxy, $(C_1-C_3)$-perfluoroalkoxy, halogen or $NR^{12}R^{13}$, in which
$R^{11}$, $R^{12}$ and $R^{13}$ are identical or different and independently of one another have the meaning mentioned for $R^5$, $R^3$ and $R^4$ are identical or different and independently of one another represent $(C_1-C_8)$-alkyl which is optionally interrupted by an oxygen or sulphur atom or by a radical $NR^{14}$ and which is optionally mono- or polysubstituted by radicals selected from the group consisting of $(C_3-C_6)$-cycloalkyl, $(C_1-C_4)$-alkoxy, halogen and $NR^{15}R^{16}$, represent $(C_3-C_8)$-cycloalkyl which is optionally interrupted by an oxygen or sulphur atom or by a radical $NR^{17}$ and which is optionally mono- or polysubstituted by radicals selected from the group consisting of $(C_1-C_4)$-alkoxy, halogen and $NR^{18}R^9$, represent aryl-$(CH_2)_p$, in which
$R^{14}$, $R^{15}$, $R^{16}$, $R^{17}$, $R^{18}$ and $R^{19}$ are identical or different and independently of one another have the meaning mentioned for $R^5$, and represents 0 or 1, or $R^3$ and $R^4$ together with the nitrogen atom form a saturated or partially unsaturated 3- to 10-membered mono- or bicyclic heterocycle which optionally contains up to two further heteroatoms selected from the group consisting of nitrogen, oxygen and sulphur and which is optionally substituted by radicals selected from the group consisting of $(C_1-C_4)$-alkyl, $(C_1-C_4)$-alkoxy, hydroxyl, halogen, $COOR^{20}$, aryl-Y and $NR^{21}R^{22}$, in which
$R^{20}$ represents hydrogen or $(C_1-C_4)$-alkyl,
Y represents a bond, $CH_2$, CO or CHOH, and
$R^{21}$ and $R^{22}$ are identical or different and independently of one another have the meaning mentioned for $R^5$, and X represents oxygen or sulphur,
and salts thereof,
except for 2-aminocarbonyl-3-methyl-5(2H)-isoxazolone.

Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, napthalenedisulphonic acid, acetic acid, propionic acid, lactic acid, tartaric acid, citric acid, fumaric acid, maleic acid or benzoic acid.

Depending on the substitution pattern, the compounds according to the invention can occur in stereoisomeric forms which are either like image and mirror image (enantiomers), or which are not like image and mirror image (diastereomers). The invention relates both to the enantiomers and the diastereomers and to their respective mixtures. The racemic forms, like the diastereomers, can be separated in a known manner into the stereoisomerically uniform components.

$(C_1-C_8)$-alkyl, $(C_1-C_6)$-alkyl or $(C_1-C_4)$-alkyl in the context of the invention represent a straight-chain or branched alkyl radical having 1 to 8, 1 to 6 and 1 to 4 carbon atoms, respectively. Examples which may be mentioned are: methyl, ethyl, n-propyl, isopropyl, tert-butyl, n-pentyl and n-hexyl. Preference is given to a straight-chain or branched alkyl radical having 1 to 4 carbon atoms $(C_1-C_4)$. Particular preference is given to a straight-chain or branched alkyl radical having 1 to 3 carbon atoms $(C_1-C_3)$.

$(C_1-C_6)$-Alkoxy in the context of the invention represents a straight-chain or branched alkoxy radical having 1 to 6 carbon atoms. Examples which may be mentioned are: methoxy, ethoxy, n-propoxy, isopropoxy, tert-butoxy, n-pentoxy and n-hexoxy. Preference is given to a straight-chain or branched alkoxy radical having 1 to 4 carbon atoms $(C_1-C_4)$. Particular preference is given to a straight-chain or branched alkoxy radical having 1 to 3 carbon atoms $(C_1-C_3)$.

Aryl in the context of the invention represents an aromatic or heteroaromatic radical having 5 to 6 ring atoms. Examples which may be mentioned are phenyl, fur-2-yl, fur-3-yl, thien-2-yl, thien-3-yl, pyrid-2-yl, pyrid-3-yl, pyrid4-yl, pyrimidin-2-yl, pyrimidin4-yl. Preference is given to phenyl. For their part, the radicals can be mono- or polysubstituted by halogen atoms, preferably chlorine or fluorine.

$(C_3-C_8)$-Cycloalkyl, $(C_3-C_6)$-cycloalkyl etc. in the context of the invention represent cyclopropyl, cyclobutyl, cyclopentyl, cyclohexyl, cycloheptyl or cyclooctyl. The following compounds may be mentioned as being preferred: cyclopropyl, cyclopentyl and cyclohexyl.

Halogen in the context of the invention generally represents fluorine, chlorine, bromine and iodine. Preference is given to fluorine, chlorine and bromine. Particular preference is given to fluorine and chlorine.

$(C_1-C_4)$-Acyl in the context of the invention represents a straight-chain or branched acyl radical having 1 to 4 carbon atoms. Examples which may be mentioned are: formyl, acetyl, propionyl, n-butyryl, iso-butyryl.

$(C_1-C_4)$-Alkoxycarbonyl in the context of the invention represents a straight-chain or branched alkoxycarbonyl radical having 1 to 6 carbon atoms. Examples which may be mentioned are: methoxycarbonyl, ethoxycarbonyl, n-propoxycarbonyl, isopropoxycarbonyl, and tert-butoxycarbonyl. Preference is given to a straight-chain or branched alkoxycarbonyl radical having 1 to 4 carbon atoms $(C_1-C_4)$. Particular preference is given to a straight-chain or branched alkoxycarbonyl radical having 1 to 3 carbon atoms $(C_1-C_3)$.

The 5- to 10-membered monounsaturated carbocycle in the context of the invention represents cyclopentene-1,2-diyl, cyclohexene-1,2-diyl, cycloheptene-1,2-diyl, cyclooctene-1,2-diyl, cyclononene-1,2-diyl or cyclodecene-1,2-diyl. Preference is given to cyclohexene-1,2-diyl, cycloheptene-1,2-diyl and cyclooctene-1,2-diyl. Individual ring atoms may be replaced by oxygen, sulphur or nitrogen atoms. Examples which may be mentioned are: 3-pyrrolin-3,4-diyl, 1,2,5,6-tetra-hydropyridin-3,4-diyl, 5,6-dihydro-(2H)-pyran-3,4-diyl.

The saturated or partially unsaturated 3- to 12-membered mono- or bicyclic heterocycle in the context of the invention represents a monocyclic or bicyclic ring having 3 to 10 ring atoms, which is attached via a nitrogen atom to the adjacent carbonyl/thiocarbonyl group and which contains up to two further heteroatoms and optionally one or more double or triple bonds. In the case of the bicycle, the two rings can be linked spirocyclically, or the bridge head atoms of the two rings are directly adjacent or separated via one to a plurality of ring atoms. Examples which may be mentioned are aziridin-1-yl, azetidin-1-yl, pyrrolidin-1-yl, pyrrolin-1-yl, piperidin-1-yl, 1,2,5,6-tetrahydropyridin-1-yl, morpholin4-yl, thiomorpholin4-yl, hexahydroazepin-1-yl, 2,3-dihydro- (1H)-indol-1-yl, octahydroindol-1-yl, 8-aza-bicyclo[3.2.1]
octan-8-yl, 3-aza-bicyclo [3.2.1]octan-3-yl, 3,8-diaza-1-
oxa-bicyclo [4.3.0]nonan-8-yl, azacyclodecene-1-yl.
Preference is given to azetidin-1-yl, pyrrolidin-1-yl and
pyrrolin-1-yl.

Preference is given to compounds of the general formula (I)
in which
  $R^1$ and $R^2$ are identical or different and
    represent $(C_1-C_8)$-alkyl which is optionally interrupted by an oxygen or sulphur atom and which is optionally mono- or polysubstituted by radicals selected from the group consisting of methoxy, ethoxy and fluorine,
    represent $(C_3-C_6)$-cycloalkyl which is optionally mono- or polysubstituted by radicals selected from the group consisting of methoxy, ethoxy and fluorine,
    represents aryl-$(CH_2)_m$,
      in which
        m represents 0, 1 or 2, or
  $R^1$ represents hydrogen, aryl-S, aryl-O, fluorine or chlorine and $R^2$ is as defined above, or
  $R^1$ and $R^2$ together with the adjacent carbon atoms form a 5- to 8-membered monounsaturated carbocycle which is optionally interrupted by an oxygen or sulphur atom and which is optionally mono- or polysubstituted by radicals selected from the group consisting of methoxy, ethoxy and fluorine,
  $R^3$ and $R^4$ are identical or different and independently of one another
    represent $(C_1-C_6)$-alkyl which is optionally interrupted by an oxygen or sulphur atom or by a radical $NR^{14}$ and which is optionally mono- or polysubstituted by radicals selected from the group consisting of cyclopropyl, cyclobutyl, methoxy, ethoxy, fluorine and $NR^{15}R^{16}$,
    represent $(C_3-C_6)$-cycloalkyl which is optionally mono- or polysubstituted by radicals selected from the group consisting of methoxy, ethoxy, fluorine and $NR^{18}R^{19}$,
    represent aryl-$(CH_2)_p$, and
      in which
        $R^{14}$, $R^{15}$, $R^{16}$, $R^{17}$, $R^{18}$ and $R^{19}$ are identical or different and represent hydrogen, $(C_1-C_3)$-alkyl, acetyl, propionyl, methoxycarbonyl or ethoxycarbonyl and
        p represents 0 or 1, or
  $R^3$ and $R^4$ together with the nitrogen atom form a saturated or partially unsaturated 4-to 9-membered mono- or bicyclic heterocycle which optionally contains up to two further heteroatoms selected from the group consisting of nitrogen, oxygen and sulphur and which is optionally substituted by radicals selected from the group consisting of methyl, ethyl, methoxy, ethoxy, hydroxyl, fluorine, $COOR^{20}$, aryl-Y or $NR^{21}R^{22}$,
    in which
      $R^{20}$ represents hydrogen, methyl or ethyl,
      Y represents a bond, $CH_2$ or CHOH, and
      $R^{21}$ and $R^{22}$ are identical or different and independently of one another represent hydrogen, $(C_1-C_3)$-alkyl, acetyl, propionyl, methoxycarbonyl or ethoxycarbonyl, and
  X represents oxygen or sulphur,
and salts thereof,
except for 2-aminocarbonyl-3-methyl-5(2H)-isoxazolone.

Particular preference is given to compounds of the general formula (I)
in which
  $R^1$ and $R^2$ are identical or different and
    represent $(C_1-C_6)$-alkyl which is optionally mono- or polysubstituted by fluorine,
    represent $(C_3-C_6)$-cycloalkyl which is optionally mono- or polysubstituted by fluorine,
    represents benzyl, or
  $R^1$ represents hydrogen, phenyl-S or phenyl-O and $R^2$ is as defined above, or
  $R^1$ and $R^2$ together with the adjacent carbon atoms form a 5- to 9-membered monounsaturated carbocycle which is optionally mono- or polysubstituted by fluorine,
  $R^3$ and $R^4$ are identical or different and independently of one another
    represent $(C_1-C_6)$-alkyl which is optionally interrupted by an oxygen or sulphur atom and which is optionally mono- or polysubstituted by radicals selected from the group consisting of $(C_3-C_6)$-cycloalkyl and fluorine,
    represent phenyl-$(CH_2)_p$,
      in which
        p represents 0 or 1, or
  $R^3$ and $R^4$ together with the nitrogen atom form a saturated or partially unsaturated 4-to 9-membered mono- or bicyclic heterocycle which optionally contains up to two further heteroatoms selected from the group consisting of nitrogen, oxygen and sulphur and which is optionally substituted by radicals selected from the group consisting of methyl, hydroxyl, fluorine, $COOR^{20}$, phenyl-Y and $NR^{21}R^{22}$,
    in which
      $R^{20}$ represents methyl,
      Y represents a bond or CHOH, and
      $R^{21}$ and $R^{22}$ are identical or different and represent hydrogen or methyl, and
  X represents oxygen,
and salts thereof,
except for 2-aminocarbonyl-3-methyl-5(2H)-isoxazolone.

Very particular preference is given to compounds according to claim 1,
where
  $R^1$ and $R^2$ are identical or different and
    represent $(C_2-C_6)$-alkyl, or
    represent cyclopentyl or cyclohexyl,
  $R^3$ and $R^4$ are identical or different and independently of one another represent methyl or ethyl, or
  $R^3$ and $R^4$ together with the nitrogen atom form an azetidin-1-yl, pyrrolidin-1-yl or pyrrolin-1-yl radical, and
  X represents oxygen,
and salts thereof.

Moreover, processes for preparing compounds of the general formula (I) have been found which are characterized in that compounds of the general formula (II)

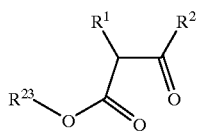

(II)

in which
R$^1$ and R$^2$ are as defined in claim 1, and
R$^{23}$ represents (C$_1$–C$_4$)-alkyl, which is optionally substituted by fluorine,
are reacted with hydroxylamine as free base or salt if appropriate in a solvent to give a compound of the general formula (III)

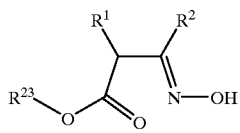

(III)

in which
R$^1$, R$^2$ and R$^{23}$ are as defined above,
which is then cyclized in the presence of a base to give a compound of the general formula (IV)

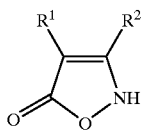

(IV)

in which
R$^1$ and R$^2$ are as defined above,
which is then reacted with a compound of the general formula (V)

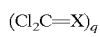

(Cl$_2$C=X)$_q$  (V)

in which
X represents oxygen or sulphur, and
q represents 1, 2 or 3,
if appropriate in the presence of an inert solvent and a base to give a compound of the general formula (VI)

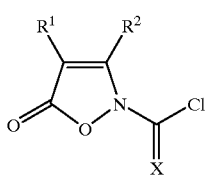

(VI)

in which,
R$^1$, R$^2$ and X are as defined above,
which are subsequently condensed with a compound of the general formula (VII)

HNR$^3$R$^4$  (VII)

in which
R$^3$ and R$^4$ are as defined in claim 1,
if appropriate in the presence of an auxiliary base to give the compound of the general formula (I).

To prepare compounds of the general formula (IV) it is also possible to use, starting from compounds of the formula (II), a one-step process without intermediate isolation of the compounds of the formula (III).

Suitable solvents for the processes are customary organic solvents which do not change under the reaction conditions. These include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, tirchloroethylene or chlorobenzene, or ethyl acetate, pyridine, dimethyl sulphoxide, N,N-dimethylformamide, hexamethylphosphoric triamide, acetonitrile, acetone or nitromethane. It is also possible to use mixtures of the solvents mentioned. Additionally, water or a mixture of water with one of the organic solvents mentioned is suitable for the processes (II)→(III) and (III)→(IV). For these processes, preference is given to water. For the processes (IV)→(VI) and (VI)→(I), preference is given to dichloromethane and trichloromethane. Particular preference is given to dichloromethane.

Suitable bases for the processes according to the invention are, in general, inorganic or organic bases. These preferably include alkali metal hydroxides, such as, for example, sodium hydroxide or potassium hydroxide, alkaline earth metal hydroxides, such as, for example, barium hydroxide, alkali metal carbonates, such as sodium carbonate, potassium carbonate or caesium carbonate, alkaline earth metal carbonates, such as calcium carbonate, or alkali metal or alkaline earth metal oxides, such as sodium methoxide or potassium methoxide, sodium ethoxide or potassium ethoxide or potassium tert-butoxide, or organic amines (trialkyl (C$_1$–C$_6$)-amines) such as triethylamine, or heterocycles, such as 1,4-diazabicyclo[2.2.2]octane (DABCO), 1,8-diazabicyclo[5.4.0]undec-7-ene (DBU), pyridine, N,N-dimethylaminopyridine, methylpiperidine or morpholine. Preference is given to sodium hydroxide for the process (II)→(III)→(IV) and to triethylamine for the process (VI)→(I).

In general, the base is employed in an amount of from 0.05 mol to 10 mol, preferably from 1 mol to 3 mol, based on 1 mole of the compound of the formula (III) or (VI).

The processes according to the invention are generally carried out in a temperature range of from –20° C. to +100° C., preferably from 0°C. to +60° C.

The processes according to the invention are generally carried out at atmospheric pressure. However, it is also possible to carry out the processes at elevated pressure or at slightly reduced pressure (for example in the range of from 0.5 to 5 bar).

The process according to the invention can be illustrated in an exemplary manner by the formula scheme below:

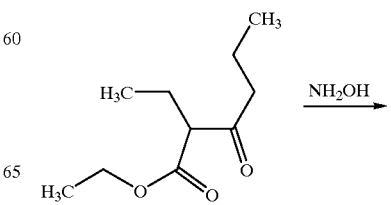

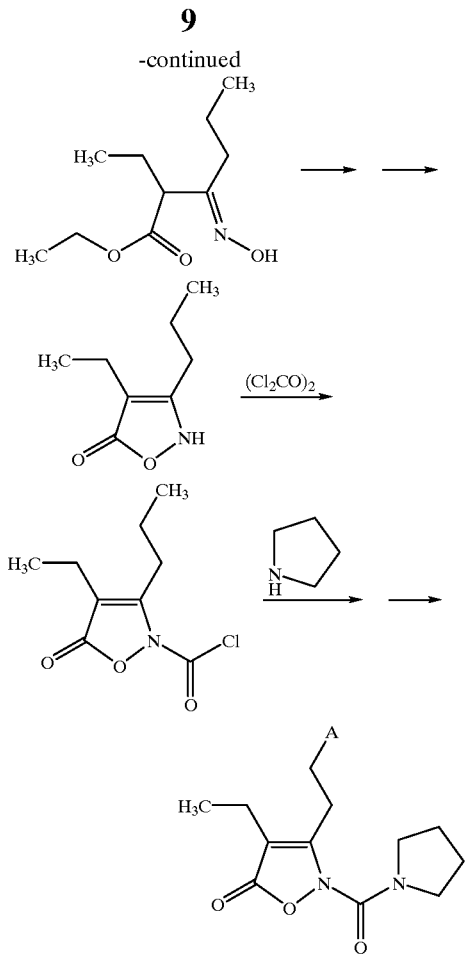

The compounds of the general formulae (II), (V) and (VII) are known or can be prepared by customary methods.

However, cognitive disturbances are not the only area of medical indication of such ligands for the newly discovered binding site. Surprisingly, it has been found that DFP also has potent action in an in vivo animal model for finding novel antidepressants. This animal model is the "Rat Forced Swimming Test" according to Porsolt (*Nature* 1977, 266, 730–732). In this test, DFP induces, in a dose-dependent manner, a behaviour-activating effect, known from clinically effective antidepressants. As in the cognition test, the optimum dosage is 0.03 mg/kg orally, i.e. far below the concentrations which would be required for cholinesterase inhibition (as described above). Based on these test results, ligands of the high-affinity DFP binding site are also suitable for use in psychiatric indications, such as, for example, depression, schizophrenia or anxiety.

The compounds according to the invention also inhibit ACPH (N-acyl-peptide hydrolase).

The novel active compounds can be converted in a known manner into the customary formulations, such as tablets, sugar-coated tablets, pills, granules, aerosols, syrups, emulsions, suspensions and solutions, using inert, non-toxic, pharmaceutically suitable excipients or solvents. Here, the therapeutically active compound should in each case be present in a concentration of about 0.0001 to 90% by weight, preferably 0.0001 to 1.0% by weight, of the total mixture, i.e. in amounts which are sufficient to achieve the dosage range indicated.

The formulations are prepared, for example, by extending the active compounds with solvents and/or excipients, if appropriate using emulsifiers and/or dispersants, it being possible, for example, if the diluent used is water, to use, if appropriate, organic solvents as auxiliary solvents.

Administration is carried out in a customary manner, preferably orally, transdermally or parenterally, in particular perlinguially or intravenously.

In general, it has proved advantageous in the case of intravenous administration to administer amounts of from approximately 0.00001 to 10 mg/kg, preferably approximately 0.0001 to 1 mg/kg, of bodyweight to achieve effective results.

In spite of this, it may be necessary, if appropriate, to depart from the amounts mentioned, namely depending on the bodyweight or on the type of administration route, on the individual response to the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide this into several individual administrations over the course of the day.

The ligands of the high-affinity DFP binding site are generally suitable for use for the prophylaxis and treatment of disorders of the central nervous system.

However, compounds of the general formula (IX)

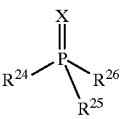

(IX)

in which
$R^{24}$ and $R^{25}$ are identical or different and independently of one another represent halogen, $(C_1-C_8)$-alkoxy, $(C_1-C_8)$-alkenoxy, aryl-S or aryl-O, where $(C_1-C_8)$-alkoxy or $(C_1-C_8)$-alkenoxy are optionally mono- or polysubstituted by halogen, and $R^{26}$ has the meaning of $R^{24}$ and is identical to or different from this meaning, or represents optionally substituted $(C_1-C_8)$-alkyl or substituted aryl, and X is as defined above are excluded.

$(C_1-C_8)$-Alkenoxy in the context of the invention represents a straight-chain or branched alkenyl-oxy radical comprising 1 to 8 carbon atoms. Examples which may be mentioned are: ethenyl, prop-2-en-1-yl, prop-2-en-2-yl, prop-3-enyl or but-1-en-1-yl.

Such novel active compounds are initially identified by an in vitro competition test at the high-affinity DFP binding site. In principle, it is also possible to employ cell membranes of other mammal species than the rat, including man, for this purpose.

For the purpose of the invention, ligands of the high-affinity DFP binding site are those substances which displace [³H]DFP when applied in a concentration of less than 10 nM with a dissociation constant $K_d$ of less than 100,000 nM.

Preference is given to ligands whose $K_d$ at this binding site is below 1000 nM. Suitable are also in particular those ligands whose binding to acetylcholinesterase is weaker by a factor of at least 500, very particularly preferably by a factor of at least 1000.

The selectivity of ligands of the high-affinity DFP binding site with respect to cholinesterase inhibition can be demonstrated using suitable in vitro tests. One such test is the photometric determination of cholinesterase activity according to Ellman (Biochem. Pharmacol. 1961, 7, 88–95).

The ligands of the high-affinity DFP binding site are particularly suitable for use for the prophylaxis and treatment of cognitive disorders, anxiety, schizophrenia or depression, very particularly of dementias of the Alzheimer type.

The effectiveness of the substances identified in this way in the treatment and prevention of cognitive disorders is confirmed with the aid of known standard animal models for learning and memory (cf., for example, *"Alzheimer's Disease: Biology, Diagnosis and Therapeutics"*, Iqbal et al., ed.; 1997, John Wiley, pp. 781–786). Animal models which are suitable for this purpose are, for example, passive or active avoidance behaviour, classic or operant conditioning, spatial orientation tests, or object or subject recognition tests. The so-called Morris test, which is based on spatial memory (*J. Neurosci. Methods* 1984, 11, 47–60), is recommended as a particularly suitable model.

1. High-affinity DFP Binding Site a) Characterization

Rat brains were homogenized in cold 50 mM tris-HCl buffer, pH 7.4, and centrifuged twice for 30 min at 48,000×g, the supernatants being discarded and the precipitate being resuspended in 50 mM tris buffer. In the binding test, the test mixture initially contained about 0.4 mg of membrane protein, various concentrations of DFP and 50 mM tris buffer. This mixture was preincubated at 25° C. in a water bath for 30 min, and commercially available [$^3$H]DFP (0.1 to 20 nM, 5 nM in standard tests) was then added. The samples were then once more mixed well and incubated at 25° C. for 120 min. After the reaction time, 3 ml of ice-cold tris buffer were added to each sample, and the membrane-bound fraction of the ligand was separated from the unbound free fraction by rapid filtration through Whatman GF/C filters. The filters were washed three times with cold buffer and the quantity of bound radio ligand was determined by β-scintillation counting. To determine specific binding, unspecific binding, determined in the presence of 100 μM of nonradioactive DFP, was subtracted from total binding.

Binding measured in this way was 90% specific and could be saturated. The apparent binding constant $K_d$, both in the total brain and in individual brain regions, such as, for example, the cerebral cortex, was 1.8±0.2 nM (mean±standard deviation of a total of 21 experiments up to 10 nM). In these experiments, the binding site density $B_{max}$ was in the range from 347±14.9 pmol/mg of membrane protein. In the range up to 10 mM of [$^3$H]DFP, the Scatchard transformation of the binding data was linear. This indicates interaction with a single non-interacting high-affinity class of binding sites for the radio ligand in this concentration range. At radio ligand concentrations of >10 nM, however, total binding increased disproportionately, indicating an interaction at higher concentrations with other binding sites having lower affinity.

b) Discrimination of the High-affinity DFP Binding Site from Cholinesterases

The DFP binding site is not a cholinesterase. Comparison of the interaction of unlabelled DFP and physiostigmine with the two biological targets under substantially identical conditions showed that DFP inhibits binding of [3H]DFP to the high-affinity binding site in rat brain membranes about 200 times more potently than acetylcholinesterase activity (IC50 11 nM vs 2.6 μM). Physiostigmine, which, like DFP, binds to the acetylcholine binding region of acetylcholinesterase, however, was only capable of inhibiting acetylcholinesterase (IC50 33 nM), but not to displace DFP from the high-affinity DFP binding site (IC50>1 mM).

c) Identification of Ligands of the High-affinity DFP Binding Site

Displacement of [$^3$H]DFP from the high-affinity DFP binding site is determined analogously to the method described under 1.a) for DFP. Example 1 showed an IC$_{50}$ of 4.8 nM.

2. Determination of the Selectivity for Acetylcholinesterase

The selectivity of the substances as DFP ligands with respect to cholinesterase inhibition can be demonstrated using suitable in vitro tests. One such test is the photometric determination of cholinesterase activity according to Ellman (Biochem. Pharmacol. 1961, 7, 88–95). In general, the experiment is carried out using crude whole brain homogenates of rats. However, suitable enzyme preparations include brain homogenates of other homeotherms including humans and also commercially available purified enzyme preparations.

In the standard experiment, rat brains are homogenized in the 20-fold volume (w/v) of 100 mM $K_2HPO_4$ buffer, pH 8.0. The protein concentration of the homogenate is adjusted to about 3 mg/ml by dilution in the buffer. The incubation mixture (1500 μl) contains 100 mM phosphate buffer pH 8.0, 330 μM dithiobisnitrobenzoate, 50 μl of brain homogenate corresponding to 150 μg of protein, various test concentrations of the test substances to be tested and 40 μM acetylthiocholine as enzyme substrate. For better comparability of the incubation conditions with those of the [$^3$H]DFP binding test, the reaction mixture is, prior to substrate addition, preincubated at room temperature for 30 min. The enzyme reaction is started by adding the substrate. The reaction time is 6 min. The samples are then admixed with 25 ml of 1 mM tacrine solution (final concentration) to stop the reaction, and the yellow dye complex is determined quantitatively in a spectrophotometer at 412 nm against the corresponding blank value (addition of tacrine prior to the additional substrate). The IC$_{50}$ is calculated from the enzyme activity in the presence of increasing concentrations of test substance in the test and compared to that for [$^3$H]DFP competition.

Example 1 inhibited acetylcholinesterase with a $K_i$ of >10 μM. Thus, the selectivity of this substance is >2000.

3. Morris Test:

The Morris test records spatial orientation learning in rodents. The test is highly suitable for evaluating the learning- and memory-enhancing action of substances. In this test, rats or mice are trained to localize a platform which they cannot see as the only way of escape from a swimming pool filled with water. It has been proven to be useful to train the animals four times per day over a period of 5 days. The test substances are administered on each day of the experiment at a defined time, for example 30 minutes before the first swim test. Controls receive the corresponding vehicle. The learning performance of the animals expresses itself in a reduction, owing to the training, of the distance swum between starting position and platform, and in a reduction of the time swum until the platform is reached, i.e. the better the animal remembers the location of the platform, the shorter the distance covered and the faster the platform is reached. The test is carried out using cognitively impaired animals, such as old animals or animals having experimentally induced brain damage.

Rats having a lesion of the entorhinal cortex are an animal model for Alzheimer's disease. The bilateral lesion of the entorhinal cortex is introduced by intracerebral injection of the excitotoxin ibotenic acid. This has a strong adverse effect on the learning performance in the Morris test.

The learning- and memory-improving effect of Example 1 was examined using this animal model. Rats having a bilateral lesion of the entorinal cortex took considerably longer to learn the platform position in the Morris test, and the performance after 5 days of training was considerably poorer than that of control animals which were operated on like the animals with lesions, but which did not receive an intracerebral injection of the excitotoxin ibotenic acid.

Intraperitoneal injection of Example 1 in a dose of 0.1 mg per kg of bodyweight 30 minutes prior to each of the five daily days of training sped up learning of the platform position considerably. Even on the second day of training, the lesioned animals treated with Example 1 achieved the same performance level as the vehicle-treated animals after 5 days of training. However, Example 1 was not capable of antagonizing the learning weakness induced by lesion of the entorhinal cortex; but with a view to the extent of the experimentally induced brain damage, this was not to be expected.

4. Rat Forced Swimming Test

The effectiveness of the substances in the treatment and prevention of affective disorders is confirmed with the aid of the "rat forced swimming tests" according to Porsolt (Nature 1977, 266, 730–732). The test is based on the observation that, in a hopeless situation, rats remain motionless ("behavioural despair"). 24 hours before the test, young adult rats (3–4 months of age) are individually placed, for 20 min, into glass cylinders (height 40 cm, diameter 20 cm) which are filled with water up to a height of 15 cm. In the test, the animals are once more transferred into the cylinder, and the duration of the immobility is measured for a period of 5 min. The test substances are administered in the period between the two swimming tests. Controls receive the corresponding vehicle.

TABLE 1

Behaviour-activating action of DFP in the "Rat forced swimming test". The behaviour effect is stated as the average change in immobility compared to vehicle-treated control animals ± standard error. The vehicle used was physiological saline. The significance of the effect was checked by ANOVA and subsequent Fischer post-hoc analysis.
n.s. = not significant.

| Dose [mg/kg p.o.] | Group size | Effect [%] | p< |
|---|---|---|---|
| Vehicle | 6 | — | — |
| 0.001 | 6 | −3.2 ± 2.2 | n.s. |
| 0.003 | 5 | −9.0 ± 2.1 | 0.05 |
| 0.01 | 6 | −11.7 ± 2.4 | 0.01 |
| 0.03 | 6 | −18.6 ± 2.9 | 0.001 |
| 0.1 | 6 | −2.9 ± 2.4 | n.s. |

Starting Compounds:

EXAMPLE I

Ethyl 2-(1-Methylpropyl)hexan-3-onecarboxylate

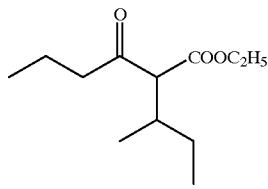

At 0°C., a solution of 10.1 g (62.5 mmol) of ethyl hexan-3-one-carboxylate in 60 ml of DMF was added dropwise to a solution of 8.84 g (68.8 mmol) of potassium tert-butoxide in 25 ml of DMF, and the mixture was then stirred at this temperature for 30 min. A solution of 7.59 ml (9.53 g, 68.1 mmol) of 2-bromobutane in 25 ml of DMF was added dropwise over a period of 30 min, and the reaction mixture was stirred at room temperature overnight. For work-up, the mixture was added to 250 ml of water and extracted with ethyl acetate (3×100 ml). The combined org. phases were dried (sodium sulphate) and concentrated, and the crude product was purified chromatographically over silica gel (0.04 to 0.63 mm) using petroleum ether: ethyl acetate 40:1.

$^1$H-NMR (DMSO, TMS, 400 MHz, δ): 4.11 (m, 2H), 3.48 (dd, 1H), 2.49 (m, 2H), 2.08 (m, 1H), 1.48 (m, 2H), 1.30 (m, 1H), 1.15 (dt, 3H), 1.10 (m, 1H), 0.84 (m, 9H); MS (DCI, NH$_3$): 215 [M+H]$^+$.

EXAMPLE II

Ethyl 2-Cyclopentylhexan-3-onecarboxylate

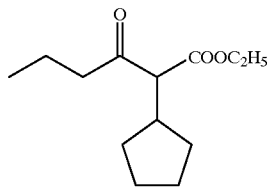

The preparation was carried out analogously to Example I from 4.04 g (25.0 mmol) of ethyl hexan-3-onecarboxylate and 2.95 ml (4.10 g, 27.3 mmol) of bromocyclopentane. Purification was carried out chromatographically (silica gel, petroleum ether: ethyl acetate 20:1). MS (EI): 226 [M]$^+$.

EXAMPLE III

Ethyl 2-Hexylhexan-3-onecarboxylate

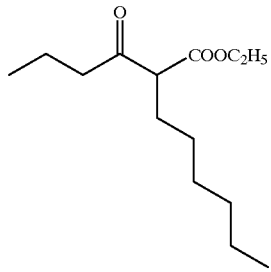

Under an atmosphere of argon, 1.59 g (69.3 mmol) of sodium were added a little at a time to 50 ml of ethanol. The mixture was then stirred under reflux until a homogeneous solution was obtained. 11.0 g (69.3 mmol) of ethyl hexan-3-onecarboxylate were added to the hot alkoxide solution, and the mixture was stirred for 45 min. 6.51 ml (7.93 g, 52.5 mmol) of 1-iodohexane were then slowly added dropwise to the boiling mixture. The mixture was stirred under reflux for 16 h, cooled to room temperature and filtered, and the solvent was then removed under reduced pressure. The residue was taken up in dichloromethane, filtered again and concentrated. The crude product was purified chromatographically (silica gel, petroleum ether: ethyl acetate 30:1). MS (DCI, NH$_3$): 309 [M+H]$^+$.

PREPARATION EXAMPLES

EXAMPLE 1

4-Ethyl-3-propyl-2-(1-pyrrolidinylcarbonyl)-5(2H)-isoxazolone

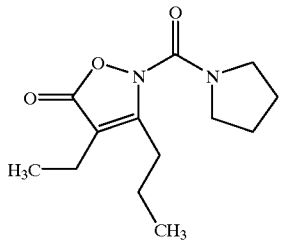

a) 4-Ethyl-3-propyl-5(2H)-isoxazolone

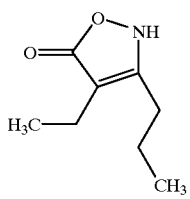

11.53 g (165.9 mmol) of hydroxylamine hydrochloride are dissolved in 25 ml of water and, at a temperature of at most 0°C., admixed with a solution of 13.27 g (331.8 mmol) of sodium hydroxide in 60 ml of water. Without further cooling, 30.9 g (165.9 mmol) of ethyl 2-ethylhexan-3-onecarboxylate are then added in one portion, and the mixture is stirred at 50° C. for 3 h. For work-up, 15.5 ml of conc. hydrochloric acid are added at 0°C., and the mixture is diluted with water and extracted three times with dichloromethane. The organic phase is dried over sodium sulphate, concentrated and fractionated under high vacuum. B.p.$^{2mbar}$ 105–115°C.

b) 4-Ethyl-3-propyl-2-(chloro-carbonyl)-5(2H)-isoxazolone

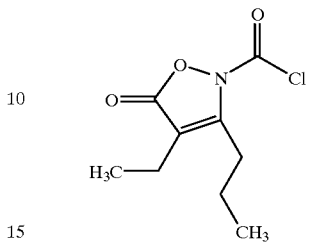

At 0° C., 15 g (96.65 mmol) of 4-ethyl-3-propyl-5(2H)-isoxazolone in 150 ml of dichloromethane are admixed with 27.81 g (144.98 mmol) of diphosgene, and the mixture is then stirred at 0° C. for 6 h. To remove excess phosgene, argon was passed through the reaction mixture at RT for 1 h, the exhaust gas being neutralized by sodium hydroxide. The solution was concentrated and the product was distilled under reduced pressure. B.p.$^{mbar}$ 125–30° C.

c) 4-Ethyl-3-propyl-2-(1-pyrrolidinylcarbonyl)-5(2H)-isoxazolone

At 0°C., a solution of 0.43 g (6 mmol) of pyrrolidine in 35 ml of dichloromethane are added dropwise to a solution of 0.44 g (2 mmol) of 4-ethyl-3-propyl-2-(chlorocarbonyl)-5(2H)-isoxazolone in 10 ml of dichloromethane, and the mixture is stirred at room temperature overnight. For work-up, the residue were chromatographed over silica gel using petroleum ether:ethyl acetate (4:1). MS (DCI): 253 (M+H).

Analogously to Example 1, the compounds of Table 2 below were prepared from the corresponding starting materials:

TABLE 2

| Example | Structure | MS(ESI): (M+H) [m/z] |
|---------|-----------|----------------------|
| 2 | 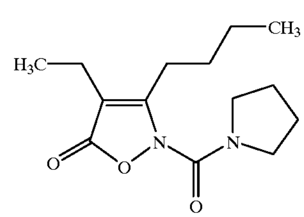 | 267 |
| 3 | 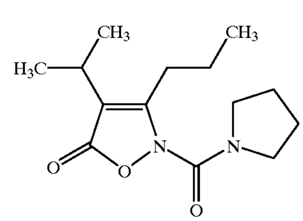 | 267 |

TABLE 2-continued

| Example | Structure | MS(ESI): (M+H) [m/z] |
|---|---|---|
| 4 | 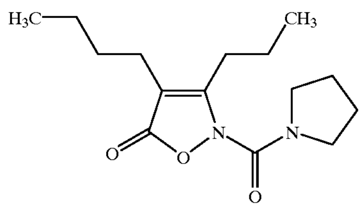 | 281 |
| 5 | 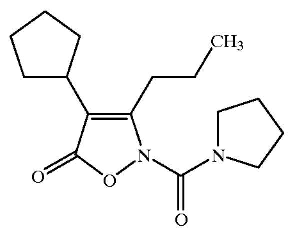 | 293 |
| 6 | 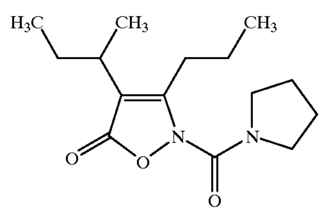 | 281 |
| 7 | 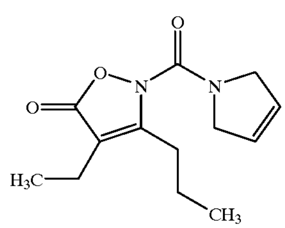 | 251 |
| 8 | 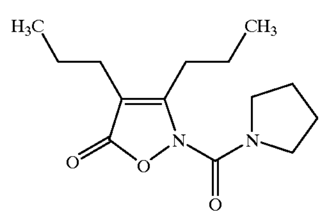 | 267 |
| 9 | 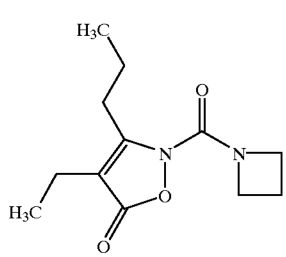 | 239 |

TABLE 2-continued
| Example | Structure | MS(ESI): (M+H) [m/z] |
|---------|-----------|----------------------|
| 10 | 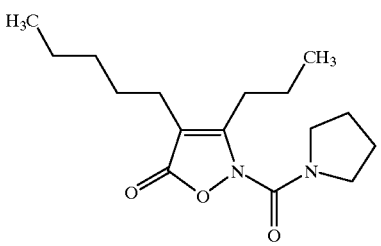 | 295 |
| 11 | 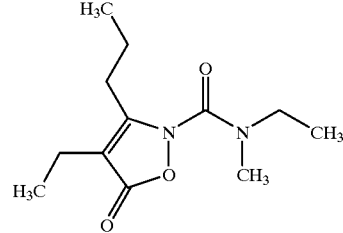 | 241 |
| 12 | 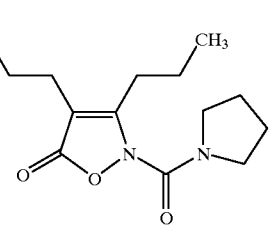 | 309 |
| 13 | 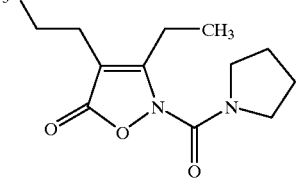 | 253 |
| 14 | 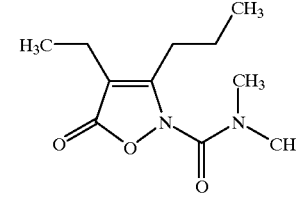 | 227 |
| 15 | 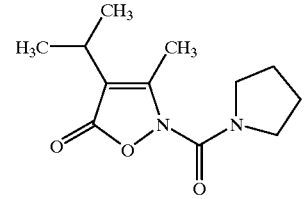 | 239 |

TABLE 2-continued

| Example | Structure | MS(ESI): (M+H) [m/z] |
|---|---|---|
| 16 | 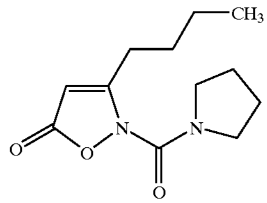 | 239 |
| 17 | 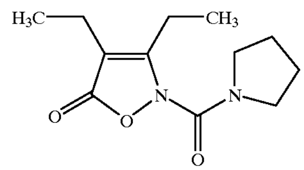 | 239 |
| 18 | 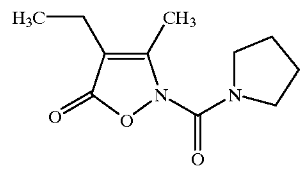 | 225 |
| 19 | 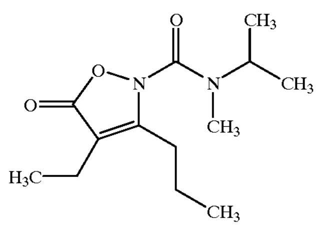 | 255 |
| 20 | 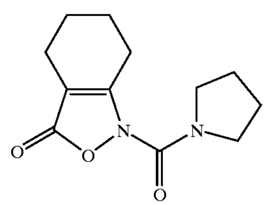 | 237 |
| 21 | 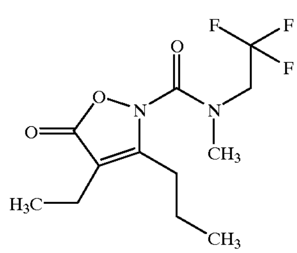 | 295 |
| 22 | 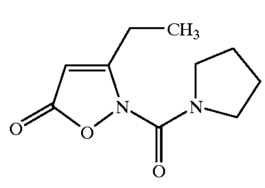 | 211 |

TABLE 2-continued

| Example | Structure | MS(ESI): (M+H) [m/z] |
|---|---|---|
| 23 | 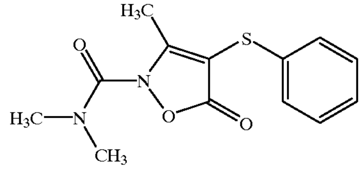 | 279 |
| 24 | 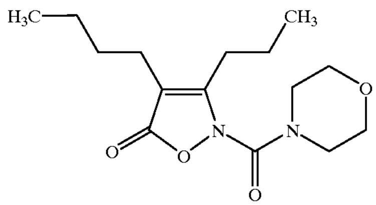 | 297 |
| 25 | 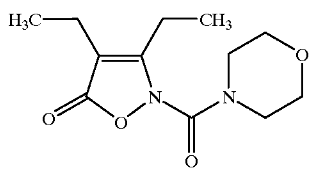 | 255 |
| 26 | 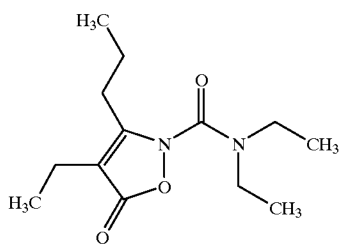 | 255 |
| 27 | 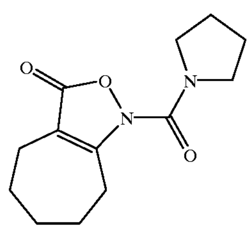 | 251 |
| 28 | 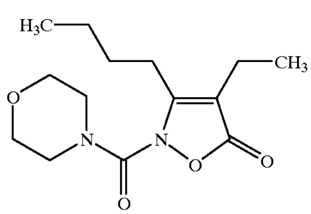 | 269 |
| 29 | 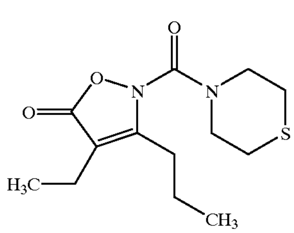 | 285 |

TABLE 2-continued

| Example | Structure | MS(ESI): (M+H) [m/z] |
|---------|-----------|----------------------|
| 30 | 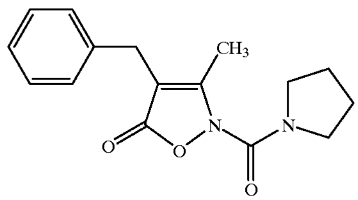 | 287 |
| 31 | 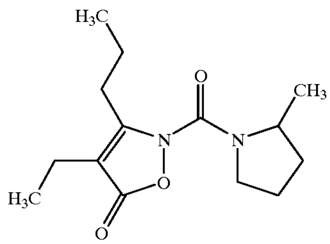 | 267 |
| 32 | 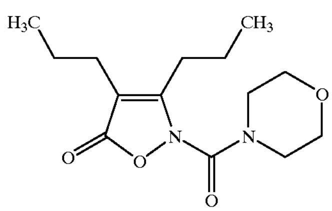 | 283 |
| 33 | 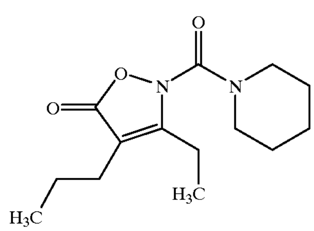 | 267 |
| 34 | 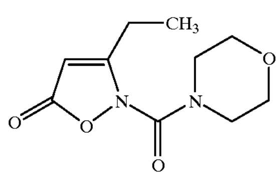 | 227 |
| 35 | 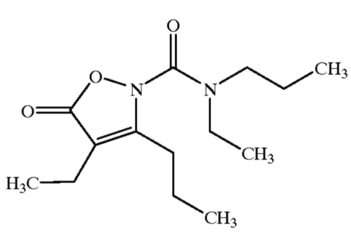 | 269 |

TABLE 2-continued

| Example | Structure | MS(ESI): (M+H) [m/z] |
|---------|-----------|----------------------|
| 36 | 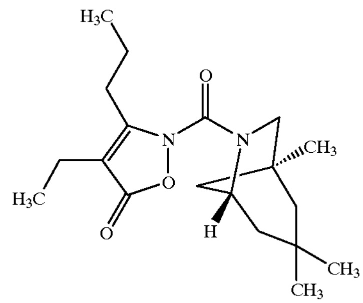 | 335 |
| 37 | 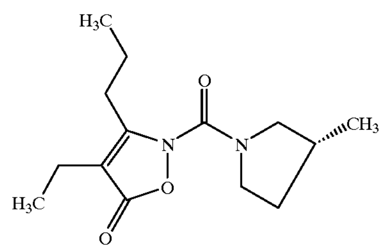 | 269 |
| 38 | 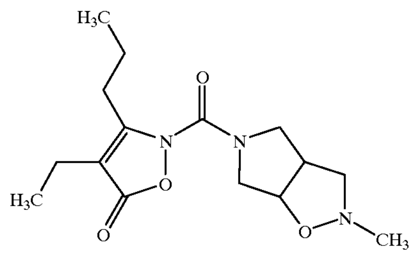 | 310 |
| 39 | 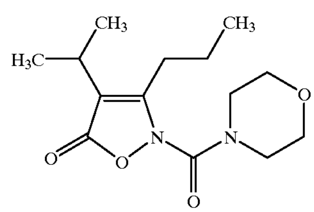 | 283 |
| 40 | 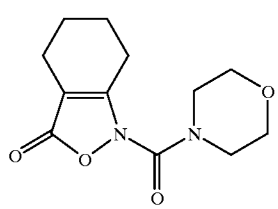 | 253 |
| 41 | 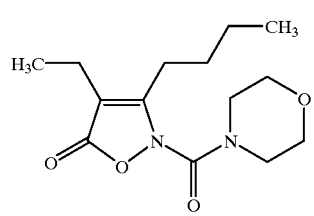 | 283 |

TABLE 2-continued

| Example | Structure | MS(ESI): (M+H) [m/z] |
|---|---|---|
| 42 | 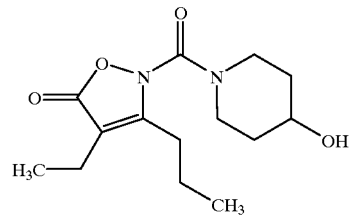 | 283 |
| 43 | 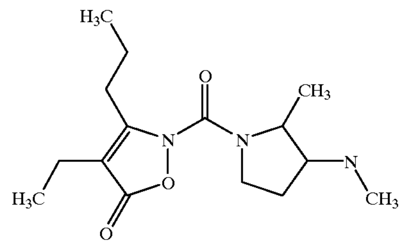 | 296 |
| 44 | 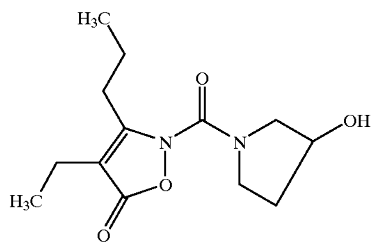 | 269 |
| 45 | 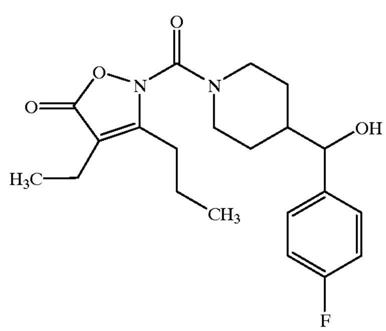 | 391 |
| 46 | 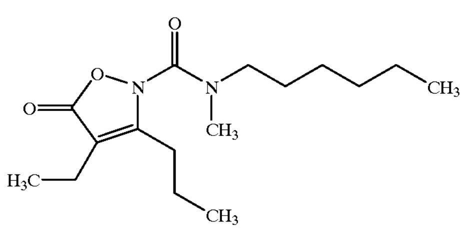 | 297 |

TABLE 2-continued

| Example | Structure | MS(ESI): (M+H) [m/z] |
|---------|-----------|----------------------|
| 47 | 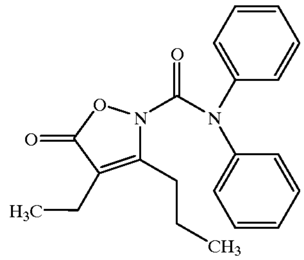 | 351 |
| 48 | 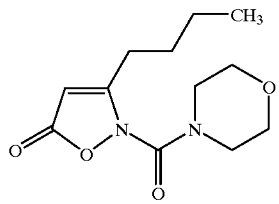 | 255 |
| 49 | 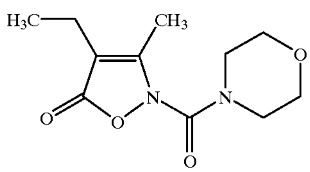 | 241 |
| 50 | 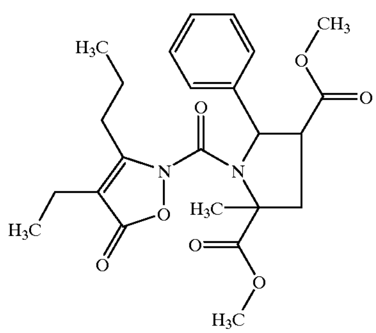 | 460 |
| 51 | 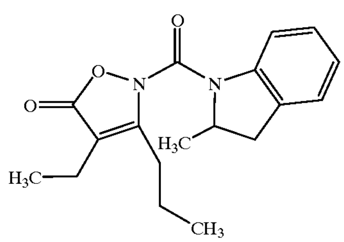 | 315 |
| 52 | 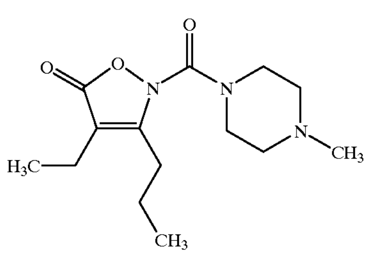 | 319 |

TABLE 2-continued

| Example | Structure | MS(ESI): (M+H) [m/z] |
|---|---|---|
| 53 | 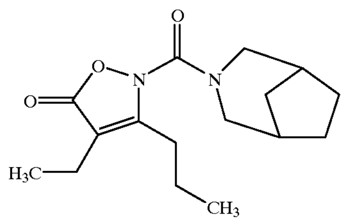 | 293 |
| 54 | 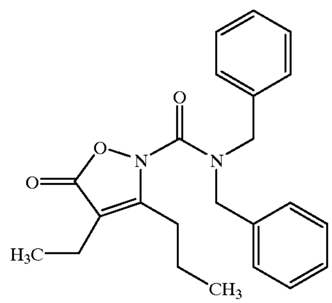 | 379 |
| 55 | 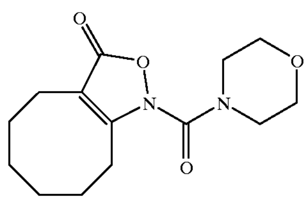 | 281 |
| 56 | 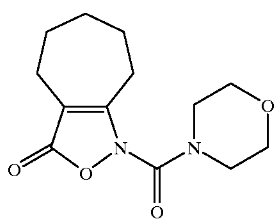 | 267 |
| 57 | 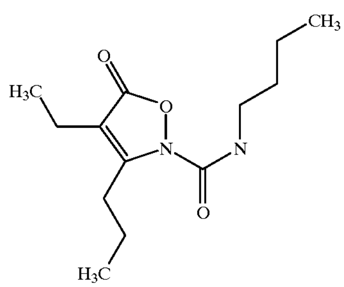 | 255 |
| 58 | 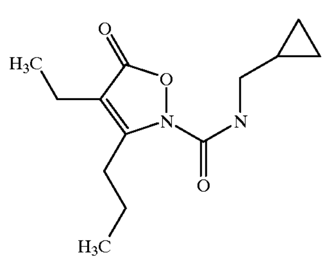 | 253 |

TABLE 2-continued

| Example | Structure | MS(ESI): (M+H) [m/z] |
|---|---|---|
| 59 | 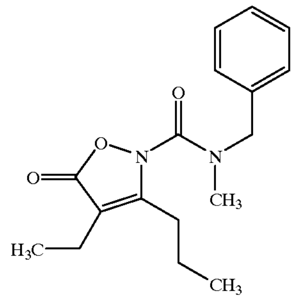 | 303 |
| 60 | 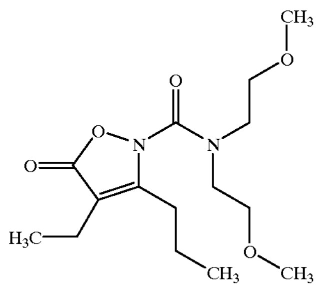 | 315 |
| 61 | 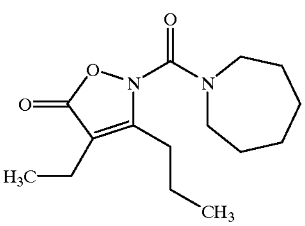 | 281 |
| 62 | 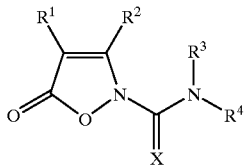 | 255 |

We claim:
1. Compounds of the general formula (I)

(I)

in which
R¹ and R² are identical or different and
represent $(C_1-C_8)$-alkyl which is optionally interrupted by an oxygen or sulphur atom or by a radical $NR^5$ and which is optionally mono- or polysubstituted by radicals selected from the group consisting of $(C_1-C_4)$-alkoxy, $(C_1-C_3)$-perfluoroalkoxy, halogen and $NR^6R^7$, represent $(C_3-C_8)$-cycloalkyl which is optionally interrupted by an oxygen or sulphur atom or by a radical $NR^8$ and which is optionally mono- or polysubstituted by radicals selected from the group consisting of $(C_1-C_4)$-alkoxy, $(C_1-C_3)$-perfluoroalkoxy, halogen and $NR^9R^{10}$, represent aryl-$(CH_2)_m$,
in which
$R^5$, $R^6$, $R^7$, $R^8$, $R^9$ and $R^{10}$ are identical or different and independently of one another represent hydrogen, $(C_1-C_4)$-alkyl, $(C_1-C_4)$-acyl, $(C_1-C_4)$-alkoxy-carbonyl, carbamoyl, mono- or di-$(C_1-C_4)$-alkyl-amino-carbonyl, and
m represents 0, 1, 2 or 3, or R¹ represents hydrogen, aryl-$S(O)_n$, $(C_1-C_4)$-alkoxy, aryl-O or halogen and $R^2$ is as defined above, and in which n represents 0, 1 or 2, or $R^1$ and $R^2$ together with the adjacent carbon atoms form a 5- to 10-membered monounsaturated carbocycle which is optionally interrupted by an oxygen or sulphur atom or by a radical $NR^{11}$ and which is optionally mono- or polysubstituted by radicals selected from the group consisting of $(C_1-C_4)$-alkoxy, $(C_1-C_3)$-perfluoroalkoxy, halogen or $NR^{12}R^{13}$, in which $R^{11}$, $R^{12}$ and $R^{13}$ are identical or different and independently of one another have the meaning mentioned for $R^5$, $R^3$ and $R^4$ are identical or different and independently of one another represent $(C_1-C_8)$-alkyl which is optionally interrupted by an oxygen or sulphur atom or by a radical $NR^{14}$ and which is optionally mono- or polysubstituted by radicals selected from the group consisting of $(C_3-C_6)$-cycloalkyl, $(C_1-C_4)$-alkoxy, halogen and $NR^{15}R^{16}$, represent $(C_3-C_8)$-cycloalkyl which is optionally interrupted by an oxygen or sulphur atom or by a radical $NR^{17}$ and which is optionally mono- or polysubstituted by radicals selected from the group consisting of $(C_1-C_4)$-alkoxy, halogen and $NR^{18}R^{19}$, represent aryl-$(CH_2)_p$, in which $R^{14}$, $R^{15}$, $R^{16}$, $R^{17}$, $R^{18}$ and $R^{19}$ are identical or different and independently of one another have the meaning mentioned for $R^5$, and p represents 0 or 1, or $R^3$ and $R^4$ together with the nitrogen atom form a saturated or partially unsaturated 3- to 10-membered mono- or bicyclic heterocycle which optionally contains up to two further heteroatoms selected from the group consisting of nitrogen, oxygen and sulphur and which is optionally substituted by radicals selected from the group consisting of $(C_1-C_4)$-alkyl, $(C_1-C_4)$-alkoxy, hydroxyl, halogen, $COOR^{20}$, aryl-Y and $NR^{21}R^{22}$, in which $R^{20}$ represents hydrogen or $(C_1-C_4)$-alkyl, Y represents a bond, $CH_2$, CO or CHOH, and $R^{21}$ and $R^{22}$ are identical or different and independently of one another have the meaning mentioned for $R^5$, and X represents oxygen or sulphur, and salts thereof, except for 2-aminocarbonyl-3-methyl-5(2H)-isoxazolone.

2. Compounds according to claim 1, where $R^1$ and $R^2$ are identical or different and represent $(C_1-C_8)$-alkyl which is optionally interrupted by an oxygen or sulphur atom and which is optionally mono- or polysubstituted by radicals selected from the group consisting of methoxy, ethoxy and fluorine, represent $(C_3-C_6)$-cycloalkyl which is optionally mono- or polysubstituted by radicals selected from the group consisting of methoxy, ethoxy and fluorine, represents aryl-$(CH_2)_m$, in which m represents 0, 1 or 2, or $R^1$ represents hydrogen, aryl-S, aryl-O, fluorine or chlorine and $R^2$ is as defined above, or $R^1$ and $R^2$ together with the adjacent carbon atoms form a 5- to 8-membered monounsaturated carbocycle which is optionally interrupted by an oxygen or sulphur atom and which is optionally mono- or polysubstituted by radicals selected from the group consisting of methoxy, ethoxy and fluorine, $R^3$ and $R^4$ are identical or different and independently of one another represent $(C_1-C_6)$-alkyl which is optionally interrupted by an oxygen or sulphur atom or by a radical $NR^{14}$ and which is optionally mono- or polysubstituted by radicals selected from the group consisting of cyclopropyl, cyclobutyl, methoxy, ethoxy, fluorine and $NR^{15}R^{16}$, represent $(C_3-C_6)$-cycloalkyl which is optionally mono- or polysubstituted by radicals selected from the group consisting of methoxy, ethoxy, fluorine and $NR^{18}R^{19}$, represent aryl-$(CH_2)_p$, and in which $R^{14}$, $R^{15}$, $R^{16}$, $R^{17}$, $R^{18}$ and $R^{19}$ are identical or different and represent hydrogen, $(C_1-C_3)$-alkyl, acetyl, propionyl, methoxycarbonyl or ethoxycarbonyl and p represents 0 or 1, or $R^3$ and $R^4$ together with the nitrogen atom form a saturated or partially unsaturated 4- to 9-membered mono- or bicyclic heterocycle which optionally contains up to two further heteroatoms selected from the group consisting of nitrogen, oxygen and sulphur and which is optionally substituted by radicals selected from the group consisting of methyl, ethyl, methoxy, ethoxy, hydroxyl, fluorine, $COOR^{20}$, aryl-Y or $NR^{21}R^{22}$, in which $R^{20}$ represents hydrogen, methyl or ethyl, Y represents a bond, $CH_2$ or CHOH, and $R^{21}$ and $R^{22}$ are identical or different and independently of one another represent hydrogen, $(C_1-C_3)$-alkyl, acetyl, propionyl, methoxycarbonyl or ethoxycarbonyl, and X represents oxygen or sulphur, and salts thereof, except for 2-aminocarbonyl-3-methyl-5(2H)-isoxazolone.

3. Compounds according to claim 1, where $R^1$ and $R^2$ are identical or different and represent $(C_1-C_6)$-alkyl which is optionally mono- or polysubstituted by fluorine, represent $(C_3-C_6)$-cycloalkyl which is optionally mono- or polysubstituted by fluorine, represents benzyl, or $R^1$ represents hydrogen, phenyl-S or phenyl-O and $R^2$ is as defined above, or $R^1$ and $R^2$ together with the adjacent carbon atoms form a 5- to 9-membered monounsaturated carbocycle which is optionally mono- or polysubstituted by fluorine, $R^3$ and $R^4$ are identical or different and independently of one another represent $(C_1-C_6)$-alkyl which is optionally interrupted by an oxygen or sulphur atom and which is optionally mono- or polysubstituted by radicals selected from the group consisting of $(C_3-C_6)$-cycloalkyl and fluorine, represent phenyl-$(CH_2)_p$, in which p represents 0 or 1, or R³ and R⁴ together with the nitrogen atom form a saturated or partially unsaturated 4- to 9-membered mono- or bicyclic heterocycle which optionally contains up to two further heteroatoms selected from the group consisting of nitrogen, oxygen and sulphur and which is optionally substituted by radicals selected from the group consisting of methyl, hydroxyl, fluorine, COOR²⁰, phenyl-Y and NR²¹R²², in which
- R²⁰ represents methyl,
- Y represents a bond or CHOH, and
- R²¹ and R²² are identical or different and represent hydrogen or methyl, and X represents oxygen,
and salts thereof,
except for 2-aminocarbonyl-3-methyl-5(2H)-isoxazolone.

4. Compounds according to claim 1,
where
- R¹ and R² are identical or different and
  represent (C₂–C₆)-alkyl, or
  represent cyclopentyl or cyclohexyl,
- R³ and R⁴ are identical or different and independently of one another
  represent methyl or ethyl, or
- R³ and R⁴ together with the nitrogen atom form an azetidin-1-yl, pyrrolidin-1-yl or pyrrolin-1-yl radical, and X represents oxygen,
and salts thereof.

5. 4-Ethyl-3-propyl-2-(1-pyrrolidinylcarbonyl)dihydro-5(2H)-isoxazolone

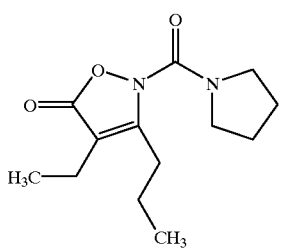

6. Process for preparing compounds according to claim 1, characterized in that compounds of the general formula (II)

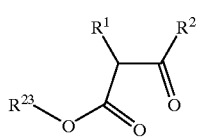
(II)

in which
- R¹ and R² are as defined in claim 1, and
- R²³ represents (C₁–C₄)-alkyl, which is optionally substituted by fluorine, are reacted with hydroxylamine as free base or salts to give a compound of the general formula (III)

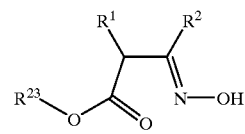
(III)

in which
R¹, R² and R²³ are as defined above,
which is then cyclized in the presence of a base to give a compound of the general formula (IV)

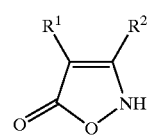
(IV)

in which
R¹ and R² are as defined above,
which is then reacted with a compound of the general formula (V)

$(Cl_2C=X)_q$ (V)

in which
X represents oxygen or sulphur, and
q represent 1, 2 or 3,
to give a compound of the general formula (VI)

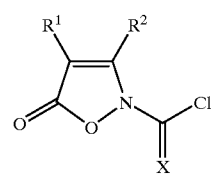
(VI)

in which
R¹, R² and X are as defined above,
which are subsequently condensed with a compound of the general formula (VII)

HNR³R⁴ (VII)

in which
R³ and R⁴ are as defined in claim 1.

7. Medicaments, comprising a compound of the general formula (I) according to claim 1 in a mixture with at least one pharmaceutically acceptable, essentially non-toxic carrier or excipient.

8. A method of treating and/or preventing a disorder of the central nervous system, comprising administering to a mammal in need thereof an effective amount of a compound according to claim 1.

9. The method of claim 8, wherein said disorder of the central nervous system is selected from the group consisting of cognitive disorders, depression, schizophrenia and anxiety.

* * * * *